United States Patent [19]

Charnley

[11] 3,953,899

[45] May 4, 1976

[54] KNEE ARTHROPLASTY

[75] Inventor: John Charnley, Knutsford, England

[73] Assignee: Chas. F. Thackray Limited, England

[22] Filed: Apr. 16, 1974

[21] Appl. No.: 461,346

[30] Foreign Application Priority Data

May 17, 1973 United Kingdom............... 23493/73

[52] U.S. Cl................................ 3/1.911; 128/92 C
[51] Int. Cl.²........................................... A61F 1/24
[58] Field of Search......................... 3/1, 1.9–1.911;
128/92 C, 92 CA, 92 R

[56] References Cited
UNITED STATES PATENTS

| 3,715,763 | 10/1973 | Goldberg et al. | 3/1 |
| 3,765,033 | 2/1973 | Link | 3/1 |

OTHER PUBLICATIONS

"New from Zimmer USA for Total Knee Reconstruction – The Polycentric – Type Total Knee", (Advertisement), *The Journal of Bone & Joint Surgery*, Vol. 55–A, No. 3, Apr. 1973.

"U.C.I. Total Knee for Natural Motion", *The Journal of Bone & Joint Surgery*, Vol. 55–A, No. 3, Apr. 1973.

Vilallium Surgical Appliance (catalog), Austenal Medical Div., Howmet Corp., New York, N.Y., 1964.

McKeever Tibial Plateaus, No. 6958–1.

*Primary Examiner*—Ronald L. Frinks
*Attorney, Agent, or Firm*—Stevens, Davis, Miller & Mosher

[57] ABSTRACT

A knee arthroplasty having two femoral implants, each for implantation into one of the femoral condyles and having a bearing surface shaped as a segment of a right circular cylinder, and a tibial portion, in the form of one or two implants, which provides a plane bearing surface for the bearing surface of each femoral implant.

13 Claims, 7 Drawing Figures

KNEE ARTHROPLASTY

This invention relates to knee arthroplastics of the type used to replace the sliding diseased surfaces of the tibia and femur, but retaining the ligaments of the joint as the flexible mechanism holding the artificial replacement surfaces in location relative to each other.

In previous knee arthroplasties of this type most of the femoral condyle had to be cut away for a femoral component to be secured to the femur, and it was also necessary to cut away a relatively large amount of the upper end of the tibia so that a tibial component could be secured to the remainder. In these known arthroplasties the femoral component has conventionally been made of metal and the tibial component has been made of a plastics material, typically high density polyethylene. The components have been of such a size that the arthroplasty has provided the bearings surfaces throughout the full range of flexion of the knee and to do this the geometry of the arthroplasties has always been designed so as to attempt to reproduce the anatomical configuration of the natural knee-joint surfaces. In these arthroplasties the metallic femoral component has had to move on an unchanging small area of the plastics tibial component, and wear of the plastics component has thus been encouraged.

According to the present invention a knee arthroplasty comprises a femoral portion and a tibial portion, the femoral portion comprising two femoral implants each being designed for implantation into one of the femoral condyles and having a bearing surface shaped as a segment of a right circular cylinder, and the tibial portion being designed for implantation into the upper end of the tibia and presenting, for each femoral implant, a plane upper surface on which the bearing surface of the femoral implant will bear.

An arthroplasty according to the invention totally abandons any attempt to reproduce the anatomical configuration of the knee-joint surfaces, and the total volume of the arthroplasty can be made very much smaller than in any previous design. This means removal of less bone and makes it possible to perform the operation at a relatively early stage in the disease process before the capsule and ligaments and the joint have become too extensively involved in the disease. The tibial portion may be no more than one or two thin hollow metal caps to cover the tibial surfaces, so allowing conservation of subchondral bone and necessitating only minimal invasion into the spongy bone of the interior of the upper end of the tibia. The form of the femoral implants also means that only a small quantity of the femoral condyles need be removed.

As indicated above, the tibial portion may be a single member but preferably the tibial portion comprises two tibial plateaux, each tibial plateau comprising a cap for keying to the upper end of the tibia and presenting a plane upper surface on which the bearing surface of a respective one of the femoral implants will bear.

Each tibial plateau is preferably in the form of a cap having a semi-circular upper surface, a flange depending from the straight side of the upper surface and a lip turned under and inwardly round the arcuate part of the upper surface. The under-turned lip acts to retain cement beneath the tibial plateau and prevent the cement escaping behind the joint. The end flange also prevents escape of cement and is preferably formed with a slot to assist keying cement to the tibial plateau. The edge of the under turned lip is desirably chamfered to avoid sharp edges. The rim may be continued completely round the arcuate edge to join the flange and so totally prevent escape of cement from beneath the cap, or for easy manufacture a small space may be left between the flange and each end of the rim.

Preferably the femoral implants are of plastics material and the tibial plateaux are of metal, so reversing the usual uses of these materials. Thus, the site of the line of contact of the plastics material with the plane metal surface will change, so spreading the wear over a larger surface area of the plastics components.

Preferably, the length of the chord joining the extremities of the longest arc of the segmental bearing surface is from 1¼ inches (3.2 cms) to 2 inches (5.1 cms) and a particularly preferred length is about 1⅝ inches (4.1 cms). The radius of the cylinder of which the bearing surface forms a part is preferably from ¾ inch (1.9 cms) to 1½ inches (3.8 cms), more preferably from 1 inch (2.5 cms) to 1⅜ inches (3.5 cms). With femoral implants of this size properly fitted to the femoral condyles the arthroplasty will bear the load of the weight of the body only in a limited arc of about 20° to 30° from the fully extended position, i.e. the arc concerned in full load bearing when walking. In strong flexion the untouched posterior surfaces of the femoral condyles articulate with the tibial plateaux.

Each femoral implant preferably has a substantially frusto-conical cross-section in a plane radial of the cylinder, with the longer parallel side lying in the bearing surface. Preferably each of the converging side surfaces of each implant is formed with an arcuate groove drawn about the same centre as that for the bearing surface. A transverse hole may be drilled through each implant to open into the grooves on the opposite surfaces of the implant. The frusto-conical cross-sectional shape allows easy insertion and location of the femoral impant in the condyle, and the grooves and hole act as keys to locate the implant securely in the cement used in performing the operation.

The invention also extends to the individual femoral implants and tibial plateaux used in the arthroplasty.

In order that the invention may be better understood, a specific embodiment of an arthroplasty according to the invention will now be described in detail, by way of example only, with reference to the accompanying drawings, in which.

Figure 1:
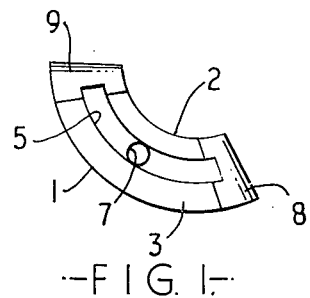
FIGS. 1 and 2 are respectively side elevations and end elevations of a femoral implant.
Figure 2:
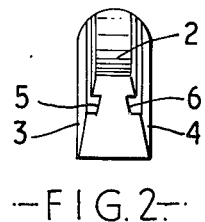
Figure 3:
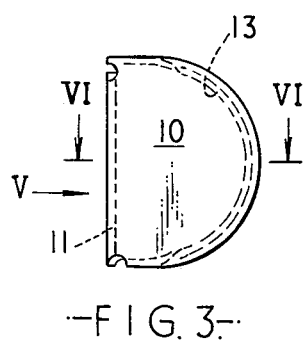
FIGS. 3 and 4 are respectively plan and underneath views of a tibial plateau.
Figure 4:
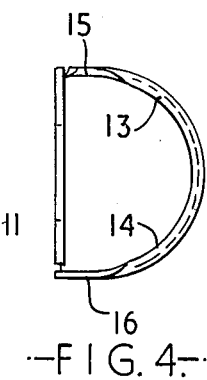
Figure 5:
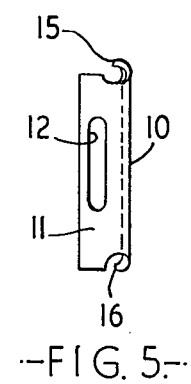
FIG. 5 is a view of the tibial plateau taken on the arrow V of FIG. 3.
Figure 6:
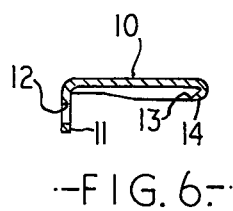
FIG. 6 is a cross-section on line VI—VI of FIG. 3.

Referring now to FIGS. 1 and 2 these show a femoral implant which is formed from a high density polyethylene. The implant has a bearing surface 1 shaped as a segment of a right circular cylinder and a further surface 2 shaped as the segment of a co-axial right circular cylinder. The implant also has converging side surfaces 3 and 4 so that a cross-section through the implant in a plane radial of the cylinder is of frusto-conical form with the longer parallel side lying in the bearing surface. Each of the converging side surfaces 3 and 4 is formed with an arcuate groove 5 and 6 respectively drawn about the same centre line as the axes of the cylinders. A transverse hole 7 is drilled through the implant to open into the grooves 5 and 6 on the opposite side surfaces of the implant. The two ends 8 and 9 of the implant are not cut in a plane radial of the cylinder but are shaped to be convex. The length of the chord joining the extremities of the longest arc of the segmental bearing surface of the implant is about 1⅝ inches (4.1 cms).

The tibial plateau shown in FIGS. 3 to 6 presents a semi-circular upper surface 10. Beneath this surface and along the straight edge thereof there is a depending flange 11 formed with a slot 12. Around the arcuate edge of the surface there is a lip 13 which is turned under and inwardly of the surface. The lip is chamfered as at 14 to provide a smooth edge to the lip. The inturned part of the lip runs into sections 15, 16 which are not inturned and which are cut away and terminate slightly short of the flange 11. The implant is made from a single sheet of metal, preferably stainless steel. It is not essential to form the chamfer for the lip, but the lip will then be of a thicker and sharper construction. In another modification the lip does not terminate short of the flange but continues right up to the flange at each side.

In a further modification the lip terminates short of the flange at one side but continues right up to the flange at the other side. Thus, referring to FIGS. 3 to 5, the lip will be cut away at section 15 but will continue right up to flange 11 at the other side. As will be described below, two such tibial plateaux are required for the knee arthroplasty and, in this last described modification, "left-handed" and "right-handed" plateaux (as viewed by the surgeon) will be provided. Where the cut-away portion is at 15 (FIG. 4) the plateau will be right-handed, and the left-handed plateau will be a mirror image of the right-handed plateau.

Figure 7:
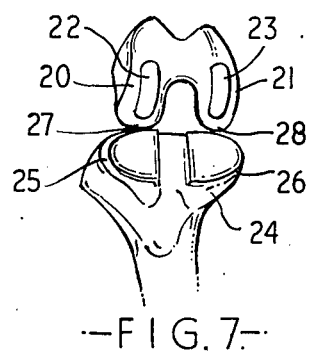
FIG. 7 shows the arthroplasty in position in a model knee joint.

In use the arthroplasty comprises two femoral implants and two tibial plateaux as shown in FIG. 7. The diseased tissue is cut away from the two femoral condyles 20, 21, the cuts being made of such a shape as to receive the femoral implants 22, 23. The implants are then inserted into the cut recesses and are bonded in position by conventional arcylic cement. Both ends of the femoral implants are visible throughout the operation and this assists in avoiding the extrusion of cement from either the posterior or anterior ends of the implants. The implants are set as shown in FIG. 7 so that they do not extend right to the posterior ends of the femoral condyles, but leave part of the natural bearing surfaces of the condyles in existence in these locations. The upper end of the tibia 24 is prepared by cutting away the diseased tissue, but preserving as much as possible of the subchondral plate of bone round the periphery. A central hole is cut into the head of the tibia in which to key cement. Each tibial plateau 25, 26 is then fitted by elevating the anterior end of the plateau from the prepared surface of the tibia as the cement is inserted so causing the posterior end of the plateau to press into the bone of the tibia to close the posterior route of possible escape for the cement. The gap that is held open beneath the front of the plateau enables the cement to be rammed in between the plateau and the bone and the plateau is then pressed down on to the tibia, pivoting on the posterior part and compressing the cement into the prepared surface in the top of the tibia. The lip and the slot in the flange of each tibial plateau retain the cement beneath the plateau and prevent the plateau from rising off the cement when this has firmly set and has bonded to the bone of the upper surface of the tibia.

When properly positioned it will be seen that the tibial plateaux replace the natural bearing surfaces of the tibia, and the femoral implants present bearing surfaces which lie flush and contiguous with the normal bearing areas of the femoral condyles. With this arrangement the femoral and tibial components combine to take the load of the weight of the body when the knee is in the fully extended position and also over a limited arc of flexion, ideally about 30° from the fully extended position. In strong flexion the untouched posterior surfaces 27, 28 of the femoral condyles will engage the bearing surface of the tibial implant.

As in the normal knee joint a small rotatory range of movement of the femoral implants on the tibial plateaux is also possible, as there is no constraint to a preformed track which favours flexion and extension.

As shown, the two tibial plateaux are individual elements and it is necessary to locate these accurately relative to each other by the use of a suitable holding jig during insertion of the implants. In a modified form of arthroplasty the two tibial plateaux can be joined together by a metal bar extending between the two plateaux and this bar may be integral with the material of the two plateaux or may be a separate element welded thereto. A holding jig is not then necessary.

Although high density polyethylene and stainless steel have been described as preferred materials for the femoral and tibial components respectively, it will be understood that those may be varied. In particular the materials used for the two components may be interchanged, the polyethylene may be replaced by some other form of plastics material and the metal may be chrome/cobalt alloy, metallic alloy or some other material which will not degrade within the body. Where a member is made out of polyethylene it may be formed by machining, forging, sintering or moulding.

As will be seen from FIG. 7 the knee arthroplasty requires removal of very much less bone than was the case in previous arthroplasties, so making this operation feasible at a much earlier stage. If by any chance the operation should not be successful it would be feasible to make a second attempt at arthroplasty by one of the existing methods involving the implant of components of much larger size.

What we claim is:

1. A knee arthroplasty comprising a femoral portion and a tibial portion, the femoral portion comprising two femoral implants each being made of plastics material and designed for implantation into one of the femoral condyles and having a bearing surface shaped as a segment of a right circular cylinder, and the tibial portion being made of metal and designed for implantation into the upper end of the tibia and presenting, for each femoral implant, a plane upper surface on which the bearing surfaces of the femoral implant will bear, said tibial portion comprising two caps, each cap having a semicircular upper surface and a lip turned under and inwardly round the arcuate part of the upper surface.

2. A knee arthroplasty according to claim 1 in which the edge of the under-turned lip is chamfered.

3. A knee arthroplasty according to claim 1 in which each cap has a flange depending from the straight side of the upper surface and the lip terminates short of the flange to leave small spaces between the flange and each end of the lip.

4. A knee arthroplasty according to claim 1 in which the length of the chord joining the extremities of the longest arc of the segmental bearing surface of each femoral implant is from 1¼ inches (3.2 cms) to 2 inches (5.1 cms).

5. A knee arthroplasty according to claim 4 in which the length of the chord of each femoral implant is about 1⅝ inches (4.1 cms).

6. A knee arthroplasty according to claim 1 in which each femoral implant has a substantially frusto-conical cross-section in a plane radial of the cylinder, with the longer parallel side lying in the bearing surface.

7. A knee arthroplasty according to claim 6 in which each of the converging side surfaces of each implant is formed with an arcuate groove drawn about the same centre as that for the bearing surface.

8. A knee arthroplasty according to claim 7 in which a transverse hole is drilled through each implant to open into the grooves in the opposite side surfaces of the implant.

9. A knee arthroplasty comprising a femoral portion and a tibial portion, the femoral portion comprising two femoral implants each being designed for implantation into one of the femoral condyles and having a bearing surface shaped as a segment of a right circular cylinder, and the tibial portion being designed for implantation into the upper end of the tibia and presenting, for each femoral implant, a plane upper surface on which the bearing surface of the femoral implant will bear, said tibial portion comprising a cap having a semicircular upper surface, a flange depending from the straight side of the upper surface and a lip turned under and inwardly round the arcuate part of the upper surface.

10. A knee arthroplasty according to claim 9 in which the tibial portion comprises two caps, each cap presenting a plane upper surface on which the bearing surface of a respective one of the femoral implants will bear.

11. A knee arthroplasty according to claim 9 in which the edge of the under-turned lip is chamfered.

12. A knee arthroplasty according to claim 10 in which the lip terminates short of the flange to leave small spaces between the flange and each end of the lip.

13. A knee arthroplasty according to claim 9 in which the two femoral implants are each made of plastics material and the tibial portion is made of metal.

* * * * *